US008771990B2

(12) United States Patent
Leng et al.

(10) Patent No.: US 8,771,990 B2
(45) Date of Patent: Jul. 8, 2014

(54) METHOD OF PRODUCING LIPIDATED POLYPEPTIDES

(75) Inventors: Chih-Hsiang Leng, Zhunan Town (TW); Chi-Ling Tseng, Zhunan Town (TW); Shih-Jen Liu, Zhunan Town (TW); Hsin-Wei Chen, Zhunan Town (TW); Pele Choi-Sing Chong, Zhunan Town (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 13/296,558

(22) Filed: Nov. 15, 2011

(65) Prior Publication Data

US 2012/0122154 A1    May 17, 2012

Related U.S. Application Data

(60) Provisional application No. 61/413,588, filed on Nov. 15, 2010.

(51) Int. Cl.
  *C12P 21/02* (2006.01)
  *C12N 1/21* (2006.01)

(52) U.S. Cl.
  USPC ............................ 435/71.3; 435/252.33

(58) Field of Classification Search
  None
  See application file for complete search history.

(56) References Cited

U.S. PATENT DOCUMENTS

| | | | |
|---|---|---|---|
| 4,745,069 | A | 5/1988 | Mayne et al. |
| 5,942,236 | A | 8/1999 | Lobert et al. |
| 6,013,258 | A | 1/2000 | Urban et al. |
| 6,183,746 | B1 | 2/2001 | Urban et al. |
| 6,361,966 | B1 | 3/2002 | Walker et al. |
| 6,538,118 | B1 | 3/2003 | Huebner et al. |
| 6,582,704 | B2 | 6/2003 | Urban et al. |
| 6,936,263 | B2 | 8/2005 | Revets et al. |
| 7,097,843 | B2 | 8/2006 | Urban et al. |
| 7,235,243 | B2 | 6/2007 | Becker et al. |
| 7,314,629 | B2 | 1/2008 | Zagury et al. |
| 7,569,225 | B2 | 8/2009 | Jackson et al. |
| 7,833,776 | B2 | 11/2010 | Leng et al. |
| 2005/0276813 | A1 | 12/2005 | Muhlradt et al. |
| 2005/0281835 | A1 | 12/2005 | Yang |
| 2009/0074781 | A1 | 3/2009 | Chen et al. |
| 2009/0081253 | A1 | 3/2009 | Hanon et al. |
| 2009/0176273 | A1 | 7/2009 | Leng et al. |
| 2009/0221499 | A1* | 9/2009 | Leng et al. ............ 514/12 |
| 2010/0303849 | A1 | 12/2010 | Chen et al. |
| 2010/0322953 | A1 | 12/2010 | Leng et al. |
| 2012/0041179 | A1 | 2/2012 | Hsieh et al. |

FOREIGN PATENT DOCUMENTS

| | | |
|---|---|---|
| CA | 2183416 | 8/1995 |
| CA | 2706101 | 6/2009 |
| CN | 1793335 | 6/2006 |
| EP | 1612218 | 1/2006 |
| EP | 2058002 | 5/2009 |
| GB | 2001/029236 | 4/2011 |
| JP | 2008-113608 | 5/2008 |
| WO | 92/05248 | 4/1992 |
| WO | 92-16636 | 10/1992 |
| WO | 99/10375 | 3/1999 |
| WO | 99/57280 | 11/1999 |
| WO | WO01/00790 | 1/2001 |
| WO | 2004/052395 | 6/2004 |
| WO | 2007/199896 | 10/2007 |
| WO | 2008/079372 | 7/2008 |
| WO | 2010/148496 | 12/2010 |

OTHER PUBLICATIONS

Masconi et al., J. Biol. Chem., 284:8738-8746, Mar. 2009.*
Sivashanmugam et al., Protein Sci., 18:936-948, 2009.*
Legrain et al., Prot. Exp. and Pur., 6, 570-578, 1995.*
Klein et al., Mol. Gen. Genet. 230:230-240, 1991.*
Cote-Sierra, et al. "A New Membrane-Bound Oprl Lipoprotien Expression Vector High Prodcution of Heterologous Fusion Proteins in Gram (+) Bacteria and the Implications for Oral Vaccination" *Gene* (1998) vol. 221, pp. 25-34.
Crill, Wayne D., et al. "Monoclonal Antibodies That Blind to Domain III of Dengue Virus E Glycoprotien Are the Most Efficient Blockers of Virus Adsorption to Vero Cells" *Journal of Virology* (Aug. 2001) pp. 7769-7773.
Jackson, D.C.; et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.
Chen, Hsin-Wei, et al. "A novel technology for the production of a heterologous lipoprotein immunogen in high yield has implications for the field of vaccine design" *Vaccine* (2009) pp. 1400-1409.
Babaeipour, Valiollah, et al. "Enhancement of human granulocyte-colony stimulating factor production in recombinant E. coli using batch cultivation" *Bioprocess Biosyst Eng* (2010) pp. 591-598.
Chiung-Yi Huang. "Potential Treatment of Human Papillomavirus Associated Tumors Using Recombinant Inactive-E7 Lipoproteins." Electronic Theses & Dissertations Services; Master Programs of Life Sciences, Aug. 24, 2009. pp. 1-5.

(Continued)

*Primary Examiner* — Nancy T Vogel
(74) *Attorney, Agent, or Firm* — Cesari and McKenna, LLP

(57) ABSTRACT

A method of producing a recombinant lipidated polypeptide in *E. coli*. The method includes providing an *E. coli* host cell adapted to express a recombinant lipidated polypeptide; and culturing the *E. coli* host cell in a minimal medium under conditions that allow expression of the polypeptide in lipidated form.

12 Claims, No Drawings

(56) References Cited

OTHER PUBLICATIONS

Cullen et al., "Construction and Evaluation of a Plasmid Vector for the Expression of Recombinant Lipoproteins in *Escherichia coli*," Plasmid 49: 18-29 (2003).

De et al., "Purification and Characterization of *Streptococcis pneumoniae* palmitoylated and pneumococcal surface adhesion A expressed in *Escherichia coli*," Vaccine: 18: 1811-1821 (2000).

Dumon-Seignovert et al., The toxicity of recombinant proteins in *Escherichia coli*: a comparison of overexpression in BL21 (DE3), C41 (DE3), and C43(DE3)., Protein Expression and Purification, vol. 37, Issue 1, Sep. 2004, pp. 203-206.

*E. coli* genotypes (last viewed on Feb. 1, 2011).

Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.

Green et al., The e(P4) Outer membrane Protein of *Haemophilus influenzae*: biologic activity of Anti-e Serum and Cloning and Sequencing of the Structural Gene., Infection and Immunity, 1991, vol. 59, pp. 3191-3198.

Hsu, C-A. et at. Immunoproteomic identification of the hypothetical protein NMB1468 as a novel lipoprotein ubiquitous in *Neisseria meningitidis* with vaccine potential. Proteomics. 2008. vol. 8, pp. 2115-2125.

Kamalakkannan et al., "Bacterial Lipid Modification of Proteins for Novel Protein Engineering Applications," Protein, Engineering, Design & Selection 17(10): 721-729 (2004).

Legrain et al., "Production of Lipidated Meningococcal Transferrin Binding Protein 2 in *Escherichia coli*" Protein Expression and Purification 6:570-578 (1995).

Liu, et al. "Structure of the Human Papillomavirus E7 Oncoprotein and its Mechanism for Inactivation ofthe Retinoblastoma Tumor Suppressor", 1. Biol. Chern., Jan. 2006. vol. 281, pp. 578-586.

Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998. pp. 2103-2109.

Sung, et al. Biochemical characterizations of *Escherichia coli*-expressed protective antigen Ag473 of *Neisseria meningitides* group B., *Vaccine*. vol. 28(51) Nov. 29, 2010, pp. 8175-8182.

ExPASy—PeptideCutter http://web.expasy.ort/cgi-bin/peptide_cutter/peptidecutter.pl (Accessed Mar. 7, 2012).

Shu, et al. Core Structure of the Outer membrane Lipoprotein from *Escherichia coli* at 1.9A Resolution, (2000) vol. 299, pp. 1101-11112.

Rezwan, et al. "Lipoprotein synthesis in mycobacteria" *Microbiology*. Mar. 2007, vol. 153, pp. 652-658.

Wikman, et al. General strategies for efficient adjuvant incorporation of recombinant subunit immunogents. *Vaccine*. (2005), vol. 23, pp. 2331-2335.

Chen, W., et al. "Induction of cytotoxic T-lymphocytes and antitumor activity by a liposomal lipopeptide vaccine" *Mol. Pharm*. vol. 5, No. 3 (2008) pp. 464-471.

Chiung-Yi Huang et al. "Recombinant Lipidated HPV E7 Induces a TH-1-Biased Immune Response and Protective Immunity against Cervical Cancer in a Mouse Model," PLOS ONE, 7(7) e40970-e40970 (2012).

* cited by examiner

METHOD OF PRODUCING LIPIDATED POLYPEPTIDES

CROSS REFERENCE TO RELATED APPLICATIONS

This application claims priority to U.S. Provisional Application No. 61/413,588, filed Nov. 15, 2010, the content of which is incorporated herein by reference in its entirety.

BACKGROUND

Post-translational modification of membrane proteins with lipids appears to be ubiquitous in prokaryotic cells. Bacterial lipoproteins share the common structural feature of a consensus sequence known as lipobox, i.e., [LVI][ASTVI][GAS]C, at the processing site. See, e.g., von Heijne, Protein Eng 2: 531-534 (1989). Once they are modified with the lipid moieties at their N-termini, they are anchored to the cell surface and function as structural proteins (e.g., murein lipoprotein) or catalytic proteins (membrane-bound enzyme or transport proteins). See, e.g., Hayashi and Wu, J Bioenerg Biomembr 22: 451-471 (1990). The biosynthesis of lipoproteins in *E. coli* has been studied in detail using Braun's lipoprotein. See, e.g., Braun and Rehn, Eur J Biochem 10: 426-438 (1969). The protein is first synthesized as an unmodified prolipoprotein and then modified by the prolipoprotein diacylglyceryl transferase (Lgt). Lgt catalyzes the transfer of the diacylglyceryl moiety from phosphatidylglycerol to the thiol group of the conserved cysteine. The lipidation signal sequence of diacylglyceryl prolipoprotein is subsequently cleaved at the modified cysteine by prolipoprotein signal peptidase (LspA). Phospholipids-apolipoprotein N-acyltransferase (Lnt) catalyzes the final modification by adding a fatty acid at the N-terminal cysteine to form the mature lipoprotein.

As most of the lipoproteins are located on the bacterial cell surface, they are readily exposed to the host's immune system. The cysteine-linked diacyl lipid moiety of lipoprotein is recognized as a danger signal by the immune system. Lipoproteins are thus critical antigens for protective immunity. Application of recombinant lipoproteins as vaccine candidates has been limited by the expression level, lipid modification, and down-stream processing of the recombinant lipoproteins. Thus, there is a need for an improved method of expressing lipoproteins.

SUMMARY

This invention is based on the surprising discovery that components of a medium can affect expression of lipidated recombinant proteins in *E. coli* cultured in the medium.

Accordingly, described herein is a method of producing a recombinant lipidated polypeptide in *E. coli*. The method includes providing an *E. coli* host cell adapted to express a recombinant lipidated polypeptide; and culturing the *E. coli* host cell in a minimal medium under conditions that allow expression of the polypeptide in lipidated form, wherein the ratio of immature to mature lipoprotein (I/M ratio) of the recombinant lipidated polypeptide thus expressed is 3.9 or lower. For example, the I/M ratio can be 0.1 or lower, 0.01 or lower, or 0.001 or lower.

In some embodiments, the minimal medium can be M9 medium. The minimal medium can also lack an organic nitrogen or ferrous source, or contain 70 mM or less of phosphate. In some embodiments, the minimal medium includes glucose. The pH of the minimal medium can be between 7.0 and 8.5.

The details of one or more embodiments of the invention are set forth in the description below. Other features, objects, and advantages of the invention will be apparent from the description, and from the claims.

DETAILED DESCRIPTION

Described herein is a method for producing a lipidated polypeptide (i.e., lipoprotein) by culturing an *E. coli* host cell adapted to express the polypeptide in a minimal medium to allow expression of the polypeptide in lipidated form. Data described below demonstrate that using a minimal medium, e.g., M9 medium, increases expression of mature lipoproteins in *E. coli*.

Preferably, the *E. coli* strains used in the method described herein are resistant to the toxic effects induced by over-expression of exogenous proteins, in particular, membrane proteins. Such *E. coli* strains can be identified or generated by the methods described in U.S. Pat. No. 6,361,966. Examples of these *E. coli* strains include, but are not limited to, C43(DE3) (ECCC B96070445), C41(DE3) (ECCC B96070444), CO214(DE3), DK8(DE3)S (NCIMB 40885), and C2014 (DE3) (NCIMB 40884).

Any of the *E. coli* strains mentioned above can be used to produce a recombinant or natural lipoprotein in lipidated form. A natural lipoprotein or lipidated protein is a protein that is lipidated in its native state. In one example, the natural lipoprotein is a mycobacterial lipoprotein, e.g., a Braun lipoprotein. Exemplary Braun lipoproteins are listed in DOLOP, a database of bacterial lipoproteins. Other Braun lipoproteins can be identified based on their amino acid sequences using the lipoprotein-predicting software also provided in the DOLOP database.

As used herein, a recombinant lipoprotein or recombinant lipidated protein refers to a protein that is not lipidated in its native form, but is modified, e.g., by adding a lipoprotein signal peptide, so that it is produced in lipidated form. Lipoprotein signal peptides (or lipid signal peptides), found on natural lipoproteins, are known in the art. Useful lipoprotein signal peptides include the signal peptide of *E. coli* acriflavine-resistance protein E precursor and the signal peptide of *Neisseria meningitides* Ag473 protein. Lipoprotein signal peptides can be identified by, for example, identifying the signal peptide on natural lipoproteins (e.g., those listed in the DOLOP database).

A natural or recombinant lipoprotein can be expressed in *E. coli* via conventional recombinant technology. Briefly, a DNA fragment encoding a natural lipoprotein is obtained from its native source via, e.g., PCR amplification, and optionally modified to optimize codon usage in *E. coli*. To produce a recombinant lipoprotein, a DNA fragment encoding a protein can be fused to a nucleic acid sequence encoding a lipid signal peptide. The DNA fragment is then inserted into an *E. coli* expression vector to produce an expression plasmid. Preferably, expression of the natural or recombinant lipoprotein is driven by a strong promoter, e.g., T7, T5, T3, or SP6, which can be inducible, e.g., by IPTG. The expression plasmid is then introduced into a selected *E. coli* strain and positive transformants are cultured under suitable conditions, e.g., in M9 medium, for protein expression.

In one preferred embodiment, the *E. coli* cells adapted to express a natural or recombinant lipoprotein are cultured in M9 medium. The M9 medium can include glucose as its carbon source. In some embodiments, the M9 medium lacks an organic nitrogen source, a ferrous source, or contains 70 mM or less phosphate. A M9 medium with higher pH values (e.g., pH 7-8.5) is also preferred for expressing mature lipoprotein.

The lipoprotein thus expressed can be isolated from the *E. coli* cells and its lipidation status can be confirmed via methods known in the art, e.g., immunoblotting with an anti-lipoprotein antibody or mass spectrometry. The expression levels of immature and mature lipoproteins can be also estimated by analyzing the corresponding band density on SDS gels using densitometry and ImageJ software. The ratio of immature to mature lipoproteins (I/M ratio) can then be calculated. The methods provided herein can produce lipidated polypeptides with an I/M ratio of 3.9 or lower (e.g., 0.1, 0.01, or 0.001 or lower).

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are herein incorporated by reference in their entirety.

Example

The data described below show that culturing *E. coli* in M9 medium increases expression of mature lipoproteins in the *E. coli*. In addition to high yield of wholly modified lipoproteins, M9 medium usage is also beneficial for lipoprotein purification, as the existence of large amount of immature lipoproteins in LB medium would impact downstream purification steps. This method of producing lipidated proteins can be used, for example, for generating recombinant lipoproteins as vaccines.

(1) Materials and Methods

All chemicals were from Sigma (St. Louis, Mo., USA) and Merck (Darmstadt, Germany). Yeast extract, tryptone and casamino acids were obtained from Difco Laboratories (Detroit, Mich., USA). Enzymes for molecular cloning were from New England Biolabs, Inc. (Beverly, Mass., USA).

*E. coli* strain C43 (DE3) (Yeastern Biotech Co., Taipei, Taiwan) was used for expressing lipoproteins. The components of the media used, including Luria-Bertani broth (LB), Super broth (SB), Terrific broth (TB), 2×YT, M9 medium, and M63 medium, are listed in Table 1 below. All media were supplemented with 50 µg/ml ampicillin. Where applicable, tryptone, yeast extract, casamino acids, or ammonium chloride was used as the nitrogen source in M9 medium. To evaluate the effect of carbon source on the expression of lipoprotein, various amounts of glucose or glycerol were added to M9 medium lacking a carbon source ($_c$M9). Five conditions were tested, including $_c$M9/0.08% glucose, $_c$M9/2% glucose, $_c$M9/0.08% glycerol, $_c$M9/0.4% glycerol, and $_c$M9/2% glycerol. In order to assess the optimal conditions for lipoprotein expression, several additional parameters were also manipulated. See Table 2 below. *E. coli* growth in culture was monitored spectrophotometrically by measuring the culture's $OD_{600\ nm}$ periodically.

TABLE 1

| Media components. | | | | | | |
|---|---|---|---|---|---|---|
| | LB | TB | 2xYT | SB | M9 | M63 |
| Tryptone | 1% | 1.2% | 1.6% | 3.5% | | |
| Yeast extract | 0.5% | 2.4% | 1% | 2% | | |
| NaCl | 1% | | 0.5% | 0.5% | 9 mM | |
| K$_2$HPO$_4$ | | 54 mM | | | | |
| KH$_2$PO$_4$ | | 16.2 mM | | | 22 mM | 100 mM |
| Na$_2$HPO$_4$ | | | | | 47.8 mM | |
| (NH$_4$)$_2$SO$_4$ | | | | | | 15 mM |
| NH$_4$Cl | | | | | 19 mM | |
| MgSO$_4$ | | | | | 2 mM | 1 mM |
| FeSO$_4$ | | | | | | 0.002 mM |
| CaCl$_2$ | | | | | 0.1 mM | |
| Glucose | | | | | 0.4% | |
| Glycerol | | | | | | 0.2% |

D1E3-expressing plasmid was constructed as described previously. See Chen et al., Vaccine 27: 1400-1409 (2009). P3E3-expressing plasmid was cloned by changing the D1 sequence of the D1E3-expressing plasmid to the P3 sequence (lipid signal peptide of *E. coli* acriflavine-resistance protein E precursor). D1Plyt-expressing plasmid was engineered by replacing the E3 sequence with a truncated pneumolysin (Plyt) sequence. The expression plasmids were transformed into the *E. coli* C43 (DE3) strain. The transformed cells were grown aerobically overnight in 5 ml of LB medium at 37° C. Before inoculating into M9 medium or fresh LB medium, 100 µl of the overnight culture was harvested by centrifugation. Bacteria were then resuspended in 5 ml of fresh media and grown aerobically in the shaking incubator (200 rpm) at 37° C. After the bacteria reached late log-phase, protein expression was induced by addition of 1 mM isopropylthio-β-D-galactoside (IPTG). Cultures were incubated for additional 3 h, and 500 µl from each of the cultures was centrifuged. The cells collected were resuspended in water to an absorbance at 600 nm of ten. Five µl of the suspension was then collected and analyzed by tricine SDS-PAGE.

For SDS gel electrophoresis, cell suspension was mixed with an equal volume of sample buffer (63 mM Tris-HCl, 2% SDS, 5% 2-mercaptoethanol, 10% glycerol, 0.002% bromophenol blue, pH 6.8) and boiled for 3 min. Proteins were separated with a Bio-Rad Mini-PROTEAN 3 system (Bio-Rad Laboratories, Hercules, Calif., USA) using 16% tricine SDS-PAGE and then stained with Coomassie Brilliant Blue R-250. For immunoblot analysis, proteins were electrophoretically transferred to polyvinylidene difluoride (PVDF) membrane (Millipore, Billerica, Mass., USA). The membrane was blocked with 5% non-fat milk in Tris-buffered saline (20 mM Tris-HCl, 150 mM NaCl, pH 7.5) containing 0.1% Tween-20 (TBST) and then incubated at room temperature for 1 h with mouse anti-(His)$_6$ antibodies (Amersham Biosciences, New Territories, HK) at a 1:15000 dilution. After washing with TBST, the blot was incubated at room temperature for 1 h with horseradish peroxidase (HRP)-conjugated goat anti-mouse IgG (1:15000) (Bethyl Laboratories, Montgomery, Tex., USA). The blot was developed using Immobilon Western HRP Substrate (Millipore, Billerica, Mass., USA) and was exposed to x-ray film. For detection of the lipid signal peptide, the blot was first incubated with the anti-MKKL polyclonal antibodies (LTK BioLaboratories, Taoyuan, Taiwan) (1:2500) and then reacted with HRP-conjugated goat anti-rabbit IgG (1:5000). The anti-MKKL polyclonal antibodies were derived from rabbits immunized with ovalbumin-conjugated lipid signal peptide.

Proteins expressed in E. coli were electrophoretically transferred to a PVDF membrane after separation by 16% tricine SDS-PAGE. The blot was stained with Coomassie Brilliant Blue R-250 for 1 min and washed three times with 50% methanol/1% acetic acid. The protein band was excised from the blot and was subjected to four cycles of Edman degradation using an Applied Biosystems Model 494 Protein Sequencer (Mission Biotech Co. LTD, Taipei, Taiwan).

The expression levels of immature and mature lipoproteins were estimated by analyzing the corresponding band density on SDS gels using densitometry and were quantified with ImageJ software. The I/M ratio was then calculated.

(2) Results

The doubling times of E. coli cultured in various media and the I/M ratios of D1E3 lipoprotein expressed the E. coli are shown in Table 2 below.

The media tested included four nutrient-rich media: LB, TB, SB and 2×YT, and two nutrient-deficient media: M9 and M63. For all nutrient-rich media, two induced bands were observed using tricine SDS-PAGE, and both bands contained a $(His)_6$-tag at their C-termini. As determined by Edman degradation, the N-terminal sequence of the upper band was MKKL. This result suggested that the upper band had an incomplete lipid modification or lacked a lipid moiety. Furthermore, it was confirmed that the induced upper band could also be recognized by anti-MKKL antibodies. On the other hand, only one induced band was observed for M9 medium. Edman degradation result showed that its N-terminus was blocked, and immunoblotting demonstrated that it did not contain the D1 N-terminal sequence. Because the lipid modification in mature lipoprotein is a N-acyl-S-diacylglyceryl-cystine structure, the N-terminal acylation of proteins would result in N-terminal blockage. These data suggested that the upper band corresponded to an immature lipoprotein and the lower band corresponded to a mature lipoprotein.

The single band for M9 medium was further purified, and mass spectrometry confirmed that it was a mature rlipo-D1E3 lipoprotein (i.e., lipidated D1E3). Under the culturing conditions described above, the induced mature rlipo-D1E3 constituted approximately 17.5% of total protein. In contrast, with LB medium, the completely modified rlipo-D1E3 accounted only for 9.5% of total protein, and the immature rlipo-D1E3 accounted for about 19.4% of total protein. The specific yield of mature rlipo-D1E3 for M9 medium was 3.6 μg per mg of wet cells, which was higher than that for LB medium (i.e., 2 μg per mg of wet cells).

The effect of another nutrient-deficient medium, M63, on expression of mature lipoprotein in E. coli was investigated. Surprisingly, two forms of recombinant protein were expressed. Just like the rich media tested, an upper band and a lower band were observed via tricine SDS-PAGE. The upper band also reacted with anti-MKKL antibodies and contained a MKKL sequence, whereas the N-terminal sequence of the lower band could not be detected by Edman degradation. While the expression of mature lipoprotein in E. coli cultured in M63 medium was relatively high, the expression of immature lipoprotein was also evident.

These data suggest that nutrient-rich media are not optimal for lipoprotein expression. Additionally, data also suggest that M9 is a better nutrient-deficient medium than M69 for lipoprotein expression.

One of the differences between rich media and minimal media is the nitrogen source. Different nitrogen sources were added to M9 medium to investigate their influence on lipoprotein expression. Tryptone, yeast extracts, or casamino acids were used as the organic nitrogen source, and ammonium chloride was utilized as the inorganic nitrogen source. Expression of lipoprotein in E. coli cultured in M9 medium supplemented with different amounts of these nitrogen sources was examined. Although the doubling times of bacteria in all the media supplemented with organic nitrogen were shorter than that for M9 medium alone (see Table 2), the level of immature lipoprotein was increased significantly. Indeed, the I/M ratio increased with increasing amount of organic nitrogen. See Table 2. Addition of $NH_4Cl$ to M9 medium did not have any significant effect, except that in the presence of 1.5% $NH_4Cl$, immature lipoproteins was detected by immunoblot using anti-MKKL antibodies. The data suggest that addition of nitrogen to M9 medium increases the level of immature lipoprotein expressed.

The level of immature lipoprotein for M63 medium was higher than that for M9 medium. Since the major difference between M9 medium and M63 medium is the carbon source, the effect of carbon source on lipoprotein expression was investigated. Different amounts of glucose or glycerol were added to M9 medium lacking a carbon source ($_cM9$), and the expression of lipoprotein was examined. The doubling times of E. coli in cM9 with glucose was shorter than that in cM9 with glycerol. See Table 2. For M9 medium with glucose, only mature lipoprotein was detected. However, for M9 medium with glycerol, immature lipoprotein was observed. These data suggest that glucose is a better carbon source than glycerol for lipoprotein expression.

TABLE 2

The doubling times (DT) and the I/M ratios for different media.

| Medium | DT (min) | I/M ratio |
|---|---|---|
| LB | 31.7 ± 0.4 | 2.1 |
| SB | 30.1 ± 1.5 | 2.6 |
| TB | 30.3 ± 1.1 | 2.5 |
| 2xYT | 28.2 ± 0.2 | 1.7 |
| M9 | 75.5 ± 1.0 | <0.001[a] |
| M63 | 105.6 ± 4.8 | 0.1 |
| M9 + 0.5% yeast extract | 46.5 ± 4.3 | 0.5 |
| M9 + 2% yeast extract | 52.1 ± 1.7 | 1.9 |
| M9 + 1% tryptone | 47.4 ± 6.8 | 1.6 |
| M9 + 4% tryptone | 47.5 ± 1.1 | 3.9 |
| M9 + 1% casamino acids | 41.5 ± 1.5 | 1.0 |
| M9 + 4% casamino acids | 76.2 ± 3.9 | 2.7 |
| M9 + 0.5% $NH_4Cl$ | 93.0 ± 2.3 | <0.001 |
| M9 + 1.5% $NH_4Cl$ | 118.5 ± 6.1 | 0.02 |
| $_cM9$/0.08% glucose | 96.2 ± 4.5 | <0.001 |
| $_cM9$/2% glucose | 98.2 ± 2.5 | <0.001 |
| $_cM9$/0.08% glycerol | 104.9 ± 0.4 | <0.01[b] |
| $_cM9$/0.4% glycerol | 107.5 ± 8.1 | <0.01 |
| $_cM9$/2% glycerol | 113.0 ± 8.4 | <0.01 |
| $_pM9$/35 mM phosphate | 83.9 ± 3.8 | <0.001 |
| M9 + 25 mM NaPi | 90.2 ± 7.9 | 0.1 |
| M9 + 100 mM NaPi | 94.8 ± 3.7 | 0.2 |
| M9 + 25 mM KPi | 99.1 ± 11.4 | 0.1 |
| M9 + 100 mM KPi | 91.4 ± 5.6 | 0.3 |
| $_{Mg}$M9/0.2 mM $MgSO_4$ | 94.7 ± 3.2 | <0.001 |
| $_{Mg}$M9/20 mM $MgSO_4$ | 102.6 ± 2.9 | <0.001 |
| $_{Ca}$M9/0.01 mM $CaCl_2$ | 109.9 ± 4.3 | <0.001 |
| $_{Ca}$M9/1 mM $CaCl_2$ | 95.4 ± 3.6 | <0.001 |
| M9 + 0.002 mM $FeSO_4$ | 82.9 ± 8.4 | 0.01 |
| M9 + 0.05 mM $FeSO_4$ | 103.8 ± 3.5 | 0.01 |

TABLE 2-continued

The doubling times (DT) and the I/M ratios for different media.

| Medium | DT (min) | I/M ratio |
|---|---|---|
| $_{pH}$M9 pH 5.5 | 100.7 ± 4.2 | 0.06 |
| $_{pH}$M9 pH 6.0 | 96.7 ± 1.6 | <0.001 |
| $_{pH}$M9 pH 8.0 | 83.8 ± 0.6 | <0.001 |
| $_{pH}$M9 pH 8.5 | 104.7 ± 2.3 | <0.001 |
| LB + MES (pH 5.5) | 36.2 ± 0.2 | 1.9 |
| LB + HEPES (pH 7.0) | 35.8 ± 2.0 | 1.9 |
| LB + TAPS (pH 8.5) | 46.4 ± 1.6 | 0.5 |

Values are shown as mean ± standard error of the mean (n = 2).
$_c$M9: M9 medium lacking carbon source; $_p$M9: M9 medium lacking phosphate; $_{Mg}$M9: M9 medium lacking MgSO$_4$; $_{Ca}$M9: M9 medium lacking CaCl$_2$; $_{pH}$M9: M9 medium with different pH values.
[a]SDS-PAGE, Coomassie blue staining, and anti-MKKL antibodies could not detect any immature lipoprotein.
[b]No induced immature lipoprotein was observed by SDS-PAGE or Coomassie blue staining, but it could be detected using anti-MKKL antibodies.

Whether medium pH ranging from 5.5 to 8.5 would affect lipoprotein maturation was investigated. The expression level of rlipo-D1E3 was relatively low for acidic medium (pH 5.5 and pH 6.0), and immature lipoprotein could be detected for M9 medium at pH 5.5. The expression level of lipoprotein was similar for pH values ranging from 7.0 to 8.5. Moreover, the I/M ratio of recombinant lipoprotein for LB medium buffered at pH 5.5 and pH 7.0 was comparable. See Table 2. Interestingly, the I/M ratio was reduced when the pH value of LB medium increased to 8.5. See Table 2. These data suggest that M9 medium with higher pH values is preferable for expressing mature lipoprotein.

Whether phosphate could affect lipoprotein expression was also determined. Mixture of monobasic dihydrogen phosphate and dibasic monohydrogen phosphate was used in order to maintain the medium at pH 7.0. For M9 medium supplemented with 25 mM phosphate, immature lipoprotein was observed. With additional 100 mM phosphate, immature lipoprotein became more evident via SDS-PAGE stained with Coomassie blue, and the I/M ratio increased to approximately 0.2. In contrast, reducing the amount of phosphate in M9 medium by 50% had no effect on lipoprotein maturation.

Other ingredients in M9 or M63 medium, including CaCl$_2$, MgSO$_4$ and FeSO$_4$, were also investigated. The maturation of lipoprotein was not affected by MgSO$_4$ or CaCl$_2$. However, addition of FeSO$_4$ to M9 medium resulted in an increase of immature lipoproteins. The data demonstrate that adding phosphate and ferrous ions in the M9 medium can result in defective lipidation.

The effect of M9 medium on expression of mature lipoproteins other than rlipo-D1E3. was also investigated. The D1 sequence of Ag473 was fused with a truncated pneumolysin (Plyt), i.e., D1Plyt, and this lipoprotein was expressed in E. coli cultured in LB or M9 medium. An induced upper band and an induced lower band of recombinant D1Plyt protein were evident via SDS-PAGE for LB medium, whereas the lower band was predominant for M9 medium. The upper band corresponded to an immature lipoprotein as determined by its N-terminal sequence. The N-terminal sequence of the lower band could not be obtained, indicating that it corresponded to a mature lipoprotein. Expressed lipidated D1Plyt for M9 medium was partially purified, and the lipid modification was confirmed using MALDI-TOF. Another signal peptide, P3 of the acriflavine-resistance protein E precursor from E. coli, was fused with E3, and the P3E3 protein was expressed in E. coli cultured in LB or M9 medium. Two bands of P3E3 were observed via SDS-PAGE for LB medium, and only the lower band was observed for M9 medium. Further analysis confirmed that the upper band was the immature lipoprotein and the lower band was the mature lipoprotein. Altogether, the data show that M9 medium is generally advantageous for expressing fully modified lipoproteins in E. coli.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of producing a recombinant lipidated polypeptide in E. coli, the method comprising:
   providing an E. coli host cell adapted to express a recombinant lipidated polypeptide, wherein the E. coli host cell is C41 (DE3), C43 (DE3), DK8 (DE3)S, or C2014 (DE3) and has a nucleic acid sequence encoding the recombinant lipidated polypeptide, which contains a bacterial lipoprotein signal peptide; and
   culturing the E. coli host cell in a M9 medium under conditions that allow expression of the polypeptide in lipidated form, wherein the ratio of immature to mature lipoprotein (I/M ratio) of the recombinant lipidated polypeptide thus expressed is 0.01 or lower, the M9 medium lacking an organic nitrogen source and a ferrous source, containing 100 mM or less of phosphate and glucose as the sole carbon source, and having a pH of 7.0-8.5.

2. The method of claim 1, wherein the minimal medium contains 70 mM or less of phosphate.

3. The method of claim 1, wherein the I/M ratio is 0.001 or lower.

4. The method of claim 1, wherein the lipoprotein signal peptide includes the D1 sequence of Ag473.

5. The method of claim 1, wherein the lipoprotein signal peptide comprises the P3 sequence of the acriflavine-resistance protein E precursor.

6. The method of claim 1, wherein the nucleic acid sequence is operably linked to an inducible promoter.

7. The method of claim 6, wherein the promoter is inducible by isopropylthio-β-D-galactoside (IPTG).

8. The method of claim 1, wherein the recombinant polypeptide includes an antigen of a pathogen.

9. The method of claim 1, wherein the E. coli host cell is C43 (DE3).

10. The method of claim 8, wherein the antigen is E3 or a pneumolysin.

11. The method of claim 10, wherein the lipoprotein signal peptide includes the D1 sequence of Ag473.

12. The method of claim 10, wherein the lipoprotein signal peptide comprises the P3 sequence of the acriflavine-resistance protein E precursor.

* * * * *